United States Patent [19]

Shum et al.

[11] Patent Number: 4,558,154
[45] Date of Patent: Dec. 10, 1985

[54] OXIDATION OF ISOBUTYLENE OXIDE TO METHACRYLIC ACID AND METHACROLEIN

[75] Inventors: Wilfred P. Shum, East Windsor; John F. White, Princeton, both of N.J.; Eva M. Beals, Washington Crossing, Pa.

[73] Assignee: Atlantic Richfield Company, Los Angeles, Calif.

[21] Appl. No.: 257,675

[22] Filed: Apr. 27, 1981

[51] Int. Cl.$^4$ .................... C07C 51/21; C07C 51/23
[52] U.S. Cl. .................................. 562/537; 568/470; 568/483
[58] Field of Search ................. 562/537; 568/470, 483

[56] References Cited

U.S. PATENT DOCUMENTS 2,075,100  3/1937  Dreyfus .............................. 562/537

Primary Examiner—Werren B. Lone
Attorney, Agent, or Firm—Michael S. Jarosz

[57] ABSTRACT

A novel synthesis of methacrylic acid and methacrolein from isobutylene oxide is provided. This method includes contacting isobutylene oxide with a catalyst, preferably a heteropolyacid catalyst, in the presence of oxygen. Using this method, isobutylene oxide conversion is nearly 100% complete. Depending upon the reaction temperature selected, yields of up to about 60% methacrolein and up to about 12% methacrylic acid may be obtained. A simple, inexpensive high yield process is thus provided for producing reaction mixtures containing methacrylic acid and methacrolein.

9 Claims, 1 Drawing Figure

OXIDATION OF ISOBUTYLENE OXIDE TO METHACRYLIC ACID AND METHACROLEIN

CROSS-REFERENCE TO RELATED PATENT APPLICATIONS

The present application is related to U.S. patent application Ser. No. 258,102, now abandoned filed of even date, entitled "Vanadotungstomolybdophosphoric Acid Oxidation Catalyst", and to application Ser. No. 258,101, filed of even date, entitled "High Selectivity Process For Vapor Phase Oxydehydrogenation Of Alkanoic Acids, Such As Isobutyric Acid, Using Dawson Structure Phosphomolybdic Acid", which applications are assigned to the assignee of the present application, and which are hereby incorporated by reference as if fully set forth herein.

BACKGROUND OF THE INVENTION

The present invention relates generally to the field of syntheses of methacrylic acid and methacrolein, and more particularly to syntheses of such materials using heteropolyacid catalysts.

Methacrylic acid and methacrolein are chemical species which are fundamental to the plastics industry. Methacrylic species, such as methacrylic esters, are used in huge quantities worldwide for diverse employment in the formulation of structural, coating, aesthetic and other polymerizable resin systems. Accordingly, the efficient synthesis of methacrylic acid and other methacrylic species, such as methacrolein, is greatly desired.

Isobutylene oxide is a readily available material having the requisite carbon atom structure for transformation into methacrylic acid and methacrolein species. Such transformation, however, requires both oxidation and dehydration. Accordingly, catalytic agents which accomplish this transformation in a selective and efficient manner are highly desired.

Heteropolyacids are a recognized class of acids containing large amounts of oxygen and hydrogen, and multiple atoms of one or more elements, such as molybdenum or tungsten, surrounding one or more heteroatoms of another element, such as phosphorus. Polyanions of such acids consist primarily of octahedral $MoO_6$ or $WO_6$ groups, so that the conversion of $[MoO_4]^{2-}$ or $[WO_4]^{2-}$ into polyanions requires an increase in coordination number. Cotton and Wilkinson, "Advanced Inorganic Chemistry", 4th edition, pp. 852–861, Wiley & Sons, N.Y. (1980), disclose that heteropolyanions can be formed either by acidification of solutions containing the requisite simple anions, or by introduction of the hetero element after first acidifying the molybdate or tungstate. As indicated at Table 22-C-2 of Cotton and Wilkinson (pg. 857), various heteropolyanion formula types are known, including the well known Keggin and Dawson structures. Thus, as used herein, the term "heteropolyacids" refers to heteropolyacids and their salts, including heteropolyacids of the Keggin and Dawson structures, as well as organoheteropoly anions and heteropoly blues, as described in the aforementioned Cotton and Wilkinson article at pages 852 through 861, which publication is hereby incorporated by reference as if fully set forth herein.

It has long been known to use various heteropolyacids to catalyze certain organic reactions. For example, in U.S. Pat. No. 4,192,951, discloses vapor phase oxidation procedures utilizing various heteropolyacid catalysts, including heteropolymolybdic catalysts containing vanadium, tungsten, tantalum or niobium act, which catalysts are used in the synthesis of such compounds as maleic acid and acetic acid.

Similarily, in U.S. Pat. No. 4,146,574 entitled "Process For Preparing Heteropoly-Acids" various heteropoly-acid catalysts are disclosed. Such catalysts are described as facilitating the oxidative dehydrogenation of isobutyric acid to methacrylic acid, the oxidative dehydrogenation of methyl isobutyrate to methylmethacrylate and methacrylic acid, the oxidative dehydrogenation of isobutyraldehyde to methacrolein and methacrylic acid, the oxidation of methacrolein to methacrylic acid, and/or the oxidative dehydrogenation of methylisopropyl ketone to methylisopropenyl ketone.

Vapor phase heteropolyacid catalized reactions, such as disclosed in U.S. Pat. No. 4,146,574, are normally conducted using a mixture of gases, such as steam, oxygen, and/or nitrogen which are permitted to contact a catalytic substrate for preselected periods at preselected reaction temperatures.

SUMMARY OF THE INVENTION

The present invention provides a novel direct synthesis of methacrylic acid and methacrolein from isobutylene oxide comprising the exposure of a mixture of isobutylene oxide and oxygen to a catalyst, preferably a heteropolyacid catalyst, under appropriate reaction conditions to produce a reaction product containing varying percentages of methacrylic acid and methacrolein. The preferred process results in a nearly 100% conversion of isobutylene oxide; the reaction produces combined yields of methacrylic species in the 50–68% range.

In accordance with the preferred method of the present invention, selectivity between methacrylic acid and methacrolein may be adjusted by varying the reaction temperature. At lower temperatures, such as about 280° C., relatively greater yields of methacrolein are obtained, while at temperatures approaching 330° C. relatively greater yields of methacrylic acid are produced.

Accordingly, a primary object of the present invention is the provision of a single step synthesis of methacrylic acid and/or methacrolein from isobutylene oxide.

Another object of the present invention is the provision of a simple, vapor phase oxidation of isobutylene oxide to produce methacrolein and/or methacrylic acid.

A further object of the present invention is the provision of a heteropolyacid catalyzed method for converting isobutylene oxide into methacrylic acid and/or methacrolein.

These and other objects of the present invention will become apparent from the following, more detailed description.

DESCRIPTION OF THE PREFERRED EMBODIMENTS

Figure 1:
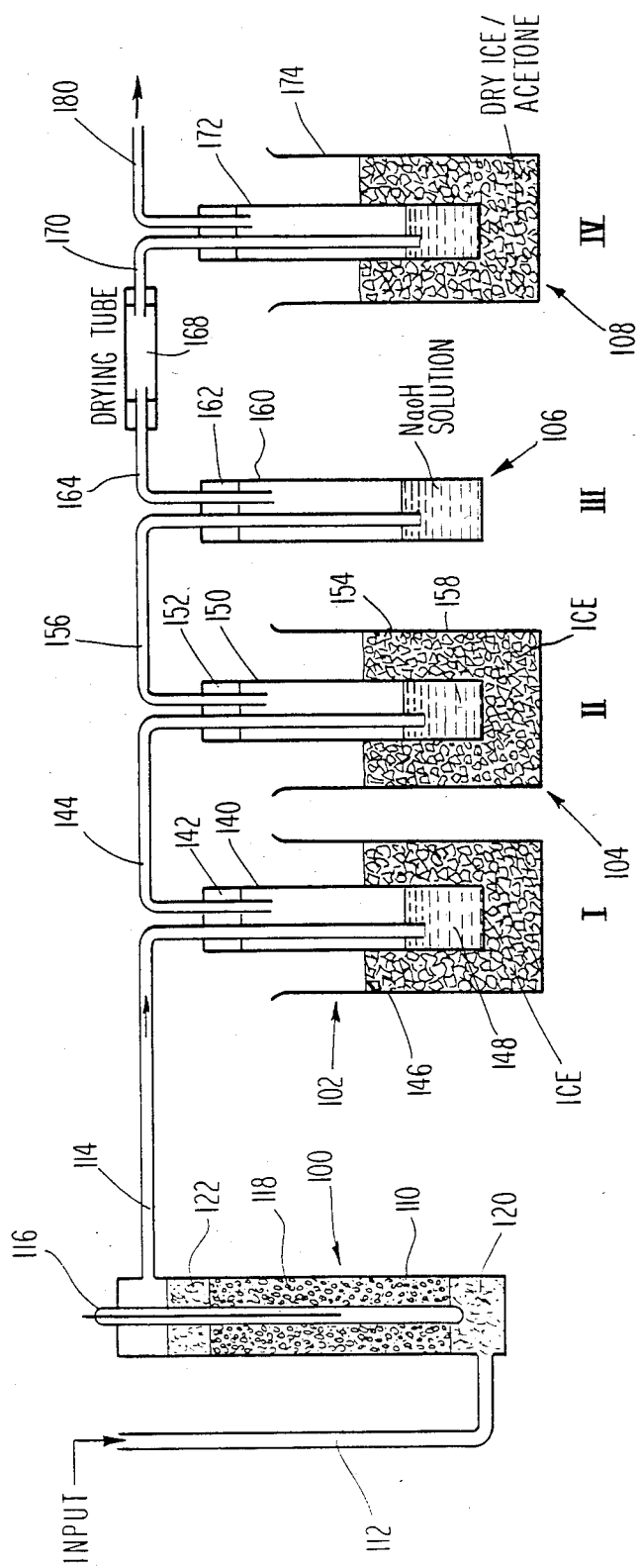
FIG. 1 is a diagram of the laboratory apparatus utilized in performing a preferred embodiment of the method of the present invention.

While particular examples have been selected in the following description for the purposes of illustration, one of ordinary skill in the art will recognize that various modifications can be made in the materials and methods described herein without departing from the scope of the present invention, which is defined more particularly in the appended claims.

While it is anticipated that the method of the present invention is useful with any of the heteropolyacid catalysts described above, the preferred catalyst for use in the present invention is 10-molybdo-2-vanadophosphoric acid which may be prepared as described by Tsigdinos and Hallada in *Inorganic Chemistry* 7, 437 (1968). In particular, this catalyst, having the empirical formula $H_5PV_2Mo_{10}O_{40}$ was prepared as follows: Sodium metavandate (24.4 grams) was dissolved in 100 milliliters of boiling water and then mixed with 7.1 grams of $Na_2HPO_4$ dissolved in 100 milliliters of water. After the solution was cooled, 5 milliliters of 98% sulfuric acid was added causing the resulting solution to develop a red color. An addition of 121 grams of $Na_2MoO_4.2H_2O$ disolved in 200 milliliters of water was then made while the solution was virgously stirred. 85 milliliters of 98% sulfuric acid was then added slowly and the hot solution allowed to cool to room temperature. The 10-molybdo-2-vanadophosphoric acid was then extracted into 500 milliliters of diethyl ether. Air was passed through the heteropoly etherate (bottom layer) to free it from ether. The solid residue was disolved in water, concentrated to first appearance of crystals in a rotary evaporator, and then allowed to crystalize further. The red, crystaline product was filtered, washed with a little cold water, and air dried. The catalyst was calcined over night at 220° C. in an automatic furnace (Thermolyne type model 2000) with a constant flow of air. The final catalyst acquired a reddish-brown color and gave a clear, red, acidic solution (pH of approximately 1) when dissolved in water.

Referring now to FIG. 1, a laboratory scale apparatus for use in performing the method of the present invention is illustrated. This apparatus comprises a reactor designated generally 100 and a series of collection traps designated generally 102, 104, 106 and 108. Reactor 100 comprises a glass reactor vessel 110 which is fed through side arm 112 and which exhausts through output conduit 114. This reactor is fitted with an axially disposed thermometer well 116. Reactor vessel 110 contains a catalyst bed 118 located within the reactor flow stream between glass bead packings 120 and 122. In a preferred embodiment, the catalyst bed comprises 50% $H_5PV_2Mo_{10}O_{40}$ deposited on a suitable silica substrate, such as Celite 408 silica which is sold by the Johns-Manville Company, Denver, Colorado. During use, the reactor is submerged in a salt bath (not shown) filled with 60% $ZnCl_2$, 20% NaCl, and 20% KCl, heated to the desired temperatures. An Isco pump model 314 was used to feed a premixed aqueous isobutylene oxide solution to a pre-heater where the liquid feed was vaporized and passed on to the catalyst bed. Oxygen and nitrogen were simultaneously fed into the reactor using a flow meter, model 10A11460, which may be obtained from Fisher and Porter.

The reaction products produced in reactor 100 were collected in the recovery train comprising traps 102, 104, 106 and 108. Condensation trap 102 comprises collection vessel 140 containing a dual port stopper 142 for receiving conduit 114 and tube 144 which are journaled therethough. Collection vessel 140 is partially immersed in ice contained within beaker 146. Reaction products 148 are thus collected by condensation within collecting vessel 140. Those products which do not condense as liquids within reaction vessel 140 are passed through tube 144 to collection trap 104, which similarly comprises collection vessel 150, stopper 152 and ice water container 154 for further fascilitating the collection of condensed reaction products 158.

As shown in FIG. 1, gaseous products not collected in trap 104 pass through conduit 156 to carbon dioxide collection trap 106. Carbon dioxide collection trap 106 similarly comprises a collection vessel 160 fitted with a dual apertured rubber stopper 162. Collection vessel 160 contains a sodium hydroxide solution for collecting carbon dioxide, the amount of which can be subsequently determined by back titrating with an acid. After passing through output tube 164 to a drying tube 168 for removing water vapor from the process stream, the stream is fed through input tube 170 to the collection vessel 172 of volatile products trap 108. Volatile products trap 108 further comprises a container 174 which holds a dry ice/acetone bath in which at least a portion of collection vessel 172 is immersed. The process stream is then vented through exhaust tube 180.

Total acids (isobutyric acid, acetic acid and methacrylic acid) recovered from traps 1 and 2 were then determined by titrating the aqueous solutions with 0.10M NaOH using phenolphthalein as the indicator. As mentioned above, carbon dioxide collected in trap III (106) was determined by back titration such as with 0.10N HCl. The reaction products collected by traps 1 and 2 were further subjected to gas chromatographic analysis to determine the percent conversion and, where appropriate, the percent selectivity of the reaction. Gas chromatographic analysis was also used to determine carbon dioxide, oxygen, and, where appropriate, carbon monoxide, using $N_2$ as the standard.

As used herein, percent conversion equals the moles of isobutylene oxide reacted divided by the moles of isobutylene oxide acid supplied times 100. In each instance, 100% conversion of isobutylene oxide was obtained. As used herein, percent selectivity refers to the number of moles of a given end product recovered divided by the number of moles of starting material (isobutylene oxide) reacted times 100. Since 100% of the isobutylene oxide utilized in the reactions described herein in fact reacted, the percent selectivity values equal the percent of given reaction product found in the reaction mixture.

Using the 50% $H_5PV_2Mo_{10}O_{40}$/Celite 408 catalyst referred to above, runs of isobutylene oxide at various temperatures were conducted, which runs are summarized in Table I:

TABLE I*

| Run # | Temp. | IBO Conversion | MAA | IBA | HOAc | MA | Acetone | HCHO | $CO_2$ |
|---|---|---|---|---|---|---|---|---|---|
| 104-24 | 278° C. | 100% | 7% | 1% | 13% | 53% | 5% | 9% | 5% |
| 104-28 | 280° C. | 100% | 8% | 1% | 13% | 60% | 5% | 3% | 6% |
| 104-30 | 280° C. | 100% | 8% | 1% | 13% | 59% | 6% | 3% | 6% |
| 104-36 | 290° C. | 100% | 9% | 1% | 11% | 54% | 6% | 3% | 7% |
| 104-40 | 300° C. | 100% | 11% | 1% | 15% | 52% | 7% | 6% | 7% |

TABLE I*-continued

| Run # | Temp. | IBO Conversion | MAA | IBA | HOAc | MA | Acetone | HCHO | CO$_2$ |
|---|---|---|---|---|---|---|---|---|---|
| 140-44 | 305° C. | 100% | 12% | 1% | 18% | 41% | 5% | 6% | 11% |
| 104-46 | 326° C. | 100% | 11% | 0% | 25% | 37% | 3% | 2% | 17% |
| 104-48 | 330° C. | 100% | 12% | 0% | 25% | 38% | 3% | 4% | 18% |

*Reaction Conditions: Feed ratio IBO/H$_2$O/O$_2$/N$_2$ = 1/75/2/8 (moles); contact time = 1 second; all percents are percents of carbon content of substrate.

As seen from Table I, methacrolein is the major product, below 300° C., with less than 10% methacrylic acid being produced at that temperature. By increasing the temperature of the reaction to 330° C., greater percentages of acetic acid and carbon dioxide are obtained while the yield of methacrylic acid increases from 7 to 12%. Since methacrolein can be readily oxidized to methacrylic acid (for example through subsequent heteropolyacid catalytic oxidation), it is presently preferred to maximize the yields of methacrylic species (methacrylic acid and methacrolein). In Table I, such species are maximized at 280° C. where such species comprise 68% of the reaction products.

From the foregoing description, one of ordinary skill in the art will recognize that the reaction of the present invention should be conducted at sufficient temperatures to facilitate the conversion of the subject substrate to the desired end product(s), but below the temperature at which substantial decomposition of the subject catalyst occurs. For example, at atmospheric pressures, the temperature of the bath in which the catalyst is contained should be maintained between about 280°-350° C., and more preferably between 280°-320° C. Additionally, the subject reactions may be run at pressures between 5-50 psig, preferably 10-30 psig. It is also preferred to use an inert diluent gas to bring the system up to proper operating pressures and to otherwise maintain favorable reaction conditions. Such inert diluents include any gas which is otherwise inert to the system, including, for example, argon, helium, nitrogen, carbon dioxide and excess steam. In any event, the subject reactions should be run with enough steam to stabilize the catalyst by, for example, maintaining the hydration of the catalyst. Contact time of the substrate with the catalyst should be controlled to achieve optimum percentages of conversion at desired selectivities. Such contact times typically range between 0.1-10 seconds preferably between 0.5-5 seconds. In performing the subject reactions, sufficient oxygen should be introduced to accomplish the desired oxidation. Generally, 0.1-25, preferably 1-12, molar equivalents of oxygen per mole of substrate should be introduced with the substrate to carry out the subject oxidation. One of ordinary skill will further recognize that various catalyst supports other than silica may be used with the disclosed catalyst. See for example, U.S. Pat. No. 4,146,574, column 3, lines 47-66, which patent is hereby incorporated by reference.

One of ordinary skill will further recognize that while a heteropolyacid catalyst is preferred, other metal oxide catalysts may be used to accomplish the subject conversion. Such catalysts include oxides of the metals of Groups IV A, V A, VI A, VII A, VIII, I B of the Periodic Table of Elements, as well, as thallium, tin, lead, arsenic, antimony, bismuth, phosphorus, cerium, uranium and thorium.

As seen from the above, a novel method for converting isobutylene oxide to a reaction product comprising methacrolein and methacrylic acid is provided, which, under preferred reaction conditions, approaches a combined yield of 70%, while producing side products comprising acetic acid, acetone, formaldehyde, carbon dioxide, and in some instances, a minor amount of isobutyric acid.

What is claimed is:

1. A method for producing methacrylic acid comprising: contacting a catalyst comprising a member selected from the group consisting of a heteropolyacid, and an oxide of a metal of Group IV A, V A, VI A, VII A, VIII, or I B of the Periodic Table of Elements, thallium, tin, lead, arsenic, antimony, bismuth, phosphorous, cerium, uranium and thorium with an isobutylene oxide vapor in the presence of oxygen to produce a reaction mixture containing said methacrylic acid.

2. The method of claim 1 wherein said catalyst is a metal oxide catalyst.

3. The method of claim 1 wherein said method is effected at a temperature between 250°-350° C.

4. The method of claim 3 wherein said temperature is between about 278°-330° C.

5. A method for producing methacrylic acid comprising contacting a mixture of isobutylene oxide vapor and oxygen in the presence of a heteropolyacid catalyst to produce a reaction mixture containing said methacrylic acid.

6. The method of claim 5 wherein said method further comprises deposition of said heteropolyacid catalyst upon a supporting surface, and said contacting is effected by introducing a regulated stream of said isobutylene oxide and said oxygen to said catalyst.

7. The method of claim 6 wherein said regulated stream further contains nitrogen.

8. The method of claim 7 wherein said method is effected at a temperature between about 278° C. and 290° C.

9. A method for producing methacrylic acid comprising contacting a mixture of isobutylene oxide vapor and oxygen in the presence of 10-molybdo-2-vanadophosphoric acid catalyst to produce a reaction mixture containing said methacrylic acid.

* * * * *